United States Patent
Hanawa et al.

(10) Patent No.: US 7,749,441 B2
(45) Date of Patent: Jul. 6, 2010

(54) AUTOMATIC ANALYZER

(75) Inventors: Masaaki Hanawa, Hitachinaka (JP); Isao Yamazaki, Ryugasaki (JP); Hitoshi Tokieda, Hitachinaka (JP); Masaharu Nishida, Hitachinaka (JP); Masaki Shiba, Hitachinaka (JP); Heino Eikmeier, Lorsch (DE); Dietmar Kappelhoff, Ketsch (DE); Christoph Möllers, Habach (DE); Stephan Sattler, Starnberg (DE)

(73) Assignees: Hitachi High-Technologies Corporation, Tokyo (JP); Roche Diagnostics Operations, Inc., Indianapolis, IN (US)

( * ) Notice: Subject to any disclaimer, the term of this patent is extended or adjusted under 35 U.S.C. 154(b) by 967 days.

(21) Appl. No.: 10/891,073

(22) Filed: Jul. 15, 2004

(65) Prior Publication Data

US 2005/0207938 A1    Sep. 22, 2005

(30) Foreign Application Priority Data

Jul. 17, 2003    (JP)    ............................ 2003-198167

(51) Int. Cl.
*G01N 35/00*    (2006.01)
*G01N 35/02*    (2006.01)
*G01N 35/04*    (2006.01)

(52) U.S. Cl. ............................ 422/64; 422/63; 422/65; 436/43; 436/45; 436/47; 436/49

(58) Field of Classification Search .................... 422/63, 422/64, 65; 436/45, 47, 48
See application file for complete search history.

(56) References Cited

U.S. PATENT DOCUMENTS

| | | | |
|---|---|---|---|
| 4,451,433 A | | 5/1984 | Yamashita et al. |
| 4,678,752 A | * | 7/1987 | Thorne et al. ............. 435/287.3 |
| 2003/0040117 A1 | * | 2/2003 | Devlin, Sr. ................... 436/46 |
| 2003/0054557 A1 | * | 3/2003 | Devlin, Sr. ................... 436/50 |
| 2004/0057872 A1 | * | 3/2004 | Shibuya et al. ............... 422/64 |
| 2004/0105783 A1 | * | 6/2004 | Yamazaki et al. ............. 422/64 |
| 2004/0253146 A1 | * | 12/2004 | Shiba et al. .................. 422/64 |
| 2005/0013735 A1 | * | 1/2005 | Gebrian et al. ................ 422/63 |

FOREIGN PATENT DOCUMENTS

| | | |
|---|---|---|
| EP | 0520304 | 12/1992 |
| EP | 1355160 | 10/2003 |
| JP | 04036658 | 2/1992 |
| JP | 3274325 | 1/2002 |
| WO | WO 02/059624 A1 * | 8/2002 |

* cited by examiner

*Primary Examiner*—P. Kathryn Wright
(74) *Attorney, Agent, or Firm*—Mattingly & Malur, P.C.

(57) ABSTRACT

An automatic analyzer is disclosed that dispenses a sample and a reagent into each of a plurality of reaction vessels to allow them to react with each other, and that measures the liquid formed as a result of the reaction. This automatic analyzer includes a first reagent storage case for storing the reagent to be used for the reaction, a second reagent storage case for storing the reagent for supplemental purpose, and a reagent conveying unit for conveying the reagent from the second reagent storage case to the first reagent storage case.

12 Claims, 5 Drawing Sheets

AUTOMATIC ANALYZER

BACKGROUND OF THE INVENTION

1. Field of the Invention

The present invention relates to an automatic analyzer that performs a quantitative/qualitative analysis of biological sample such as blood, urine, or the like, and more particularly, to a novel automatic analyzer capable of analyzing more analysis items.

2. Description of the Related Art

In the field of automatic analysis, a random access type automatic analyzer, which uses a plurality of reaction lines at random, has been developed, and has dramatically improved the processing capability of analysis. As a consequence, the consumption of reagents has speeded up and opportunities to replace reagents have increased. Also, with the advances in measurement techniques, the demand for measurements of extensive analysis items is growing. Therefore, it is desired to increase the number of reagents mountable in a reagent storage case.

In order to increase the number of mountable reagent containers, for example, Japanese Patent No. 3274325 proposes to arrange a plurality of reagent storage cases each having a circular shape in plan view in a concentric circular state, and drive the reagent storage cases independently of each other, thereby achieving an improvement in the ease-of-use thereof.

SUMMARY OF THE INVENTION

With the enhancement of the analysis speed of the apparatus, the consumption of reagents increases, and time intervals between reagent-container replacing operations have been reduced. In conventional apparatuses, once a reagent container has been set, it can be continuously used for a considerably long time period without being replaced, whereas, in recent years, it is conceivable that a reagent container set in the morning will have to be replaced on the same day. In the automatic analyzer set forth in the above-described Japanese Patent No. 3274325, when attempting to replace a reagent container, it is necessary for an operator to temporarily interrupt the measurement, take out an reagent container from a cold-storage chamber located at another place, and input information such as the kind of reagent, lot number, and the like into the automatic analyzer before setting the reagent container in the automatic analyzer. Therefore, the problem occurs that more the number of replacing operations of reagent, the less the time for analysis. In addition, there is a possibility that, when attempting to taking out a reagent from the cold-storage chamber, a reagent container other than the intended reagent container is taken out and set in error.

Accordingly, it is an object of the present invention to provide an automatic analyzer that reduces burden imposed on the operator, such as reagent registration and reagent replacing operations, and that eliminates the deficiency of a reagent during analysis, thereby minimizing the interruption of the analysis.

To achieve the above-described object, the present invention provides an automatic analyzer that dispenses a sample and a reagent into each of a plurality of reaction vessels to allow them to react with each other, and that measures the liquid formed as a result of the reaction, includes a first reagent storage case for storing a plurality of reagents and allowing each of the reagents to be dispensed from a specified position thereof; a second reagent storage case for storing a plurality of reagents for supplemental purpose; and a reagent conveying unit for conveying each of the reagents from the second reagent storage case to the first reagent storage case.

Typically, the dispensing of a sample and reagent is performed by using a dispensing nozzle for sucking/discharging a liquid making use of suction or negative pressure of a syringe, but the dispensing method in the present invention is not limited to this method using the dispensing nozzle.

The first reagent storage case stores reagents to be used for analysis, and allows them to be dispensed from a specified position. However, the reagents can be dispensed not only from a specified position, but also from a plurality of specified positions. In an extreme case, the first reagent storage case may be configured so that all the reagents can be dispensed from their respective reagent positions. Usually, the reagent dispensing position is fixed, and a reagent disk having reagent containers mounted thereon is supposed to be rotated so that it can arbitrarily move each of the reagent containers to the pertinent dispensing position. However, the dispensing system in the present invention is not restricted to this usual dispensing system.

The second reagent storage case for supplement may have a box shape, circle shape, or whatever, as long as it can mount a plurality of reagent containers. Regarding each of the reagent containers in the second reagent storage case, the reagent information, such as the storage position, kind, lot number of the pertinent reagent, is subjected to management.

Because the management of reagent information can be performed even during analysis, the reagent information either may be managed by the operator inputting it into the apparatus, or may undergo barcode management. However, taking the work load imposed upon the operator into consideration, the barcode management is preferable to the management by the operator.

Regarding each of the reagent containers used for analysis, which are stored in the first reagent storage case, the reagent information, such as the storage position, kind, lot number, remaining amount of the reagent, is subjected to management. Since the remaining amount of a reagent is subjected to management, a request to supplement the reagent is made of the second reagent storage case before the reagent becomes deficient, whereby the reagent is supplemented. Then, the reagent conveying unit takes out the designated reagent from the second reagent storage case for supplement, and disposes the reagent container in its designated position in the first reagent storage case for analysis, at a timing that allows the interruption of analysis to be minimized. Specifically, the disposition of the reagent container is performed during the time interval between a first reagent addition and a second reagent addition, or during a sample-to-sample interval, or alternatively it is performed by temporarily interrupting sampling. The information about the disposed reagent container may be taken over, or alternatively may be obtained by newly re-reading a barcode. When the barcode is to be re-read, it may be read before the reagent container is transferred from the reagent storage case for supplement to the reagent storage case for analysis, or alternatively immediately after the reagent container has been disposed. Used reagent containers in the first reagent storage case for analysis are discharged by the reagent conveying unit and disposed of.

Because the reagent container usually has a cap thereon, it must be uncapped or bored prior to reagent conveyance. Between the second reagent storage case for supplement and the first reagent storage case for analysis, there is provided an uncapping mechanism or a boring mechanism, whereby the reagent container is automatically uncapped or bored. Each of the uncapping mechanism and boring mechanism may either be a mechanism combined with the reagent conveying unit, or a stand-alone mechanism. It is desirable that the reagent container be uncapped immediately before being introduced into the first reagent case for analysis.

Since reagents mounted on the second reagent storage case might be left standing there for a long time, it is preferable that the reagents be subjected to cold-storage, allowing for their deterioration.

It is preferable that the reaction vessels be mounted on an annular reaction disk that is rotatable in one direction. Also, it is preferable that the first reagent storage case have a reagent container containing the reagent, and that the reagent containers be mounted on two annular reagent disks, the two annular reagent disks being disposed in the inner peripheral portion of the reaction disk and outside the reaction disk. Furthermore, it is preferable that the reagent containers mounted on each of the reagent disks be disposed along the outer periphery of the reagent disk in a state where they are arranged side by side in the radial direction of the reagent disk by twos or more.

The second reagent storage case according to the present invention is preferably provided above the reagent disk that is disposed outside the reaction disk, the second reagent storage case holding therein a plurality of reagent containers in a state where they are arranged in line by twos or more. Alternatively, the second reagent storage case is preferably provided above the reagent disk that is disposed outside the reaction disk so as to be rotationally drivable, the second reagent storage case holding therein a plurality of reagent containers in a state where they are arranged in an annular manner by twos or more. Still alternatively, the second reagent storage case is preferably provided on a side portion of the reagent disk that is disposed outside the reaction disk so as to be rotationally drivable in the up-and-down direction, the second reagent storage case holding therein a plurality of reagent containers in a state where they are arranged in an annular manner by twos or more.

The first reagent storage case for analysis and the second reagent storage case for supplement can be spatially separated. The reagent conveying unit may be a type using a robot arm, a type using a belt conveyor, or whatever, as long as it can convey a reagent container.

DESCRIPTION OF THE PREFERRED EMBODIMENTS

First Embodiment

Figure 1:
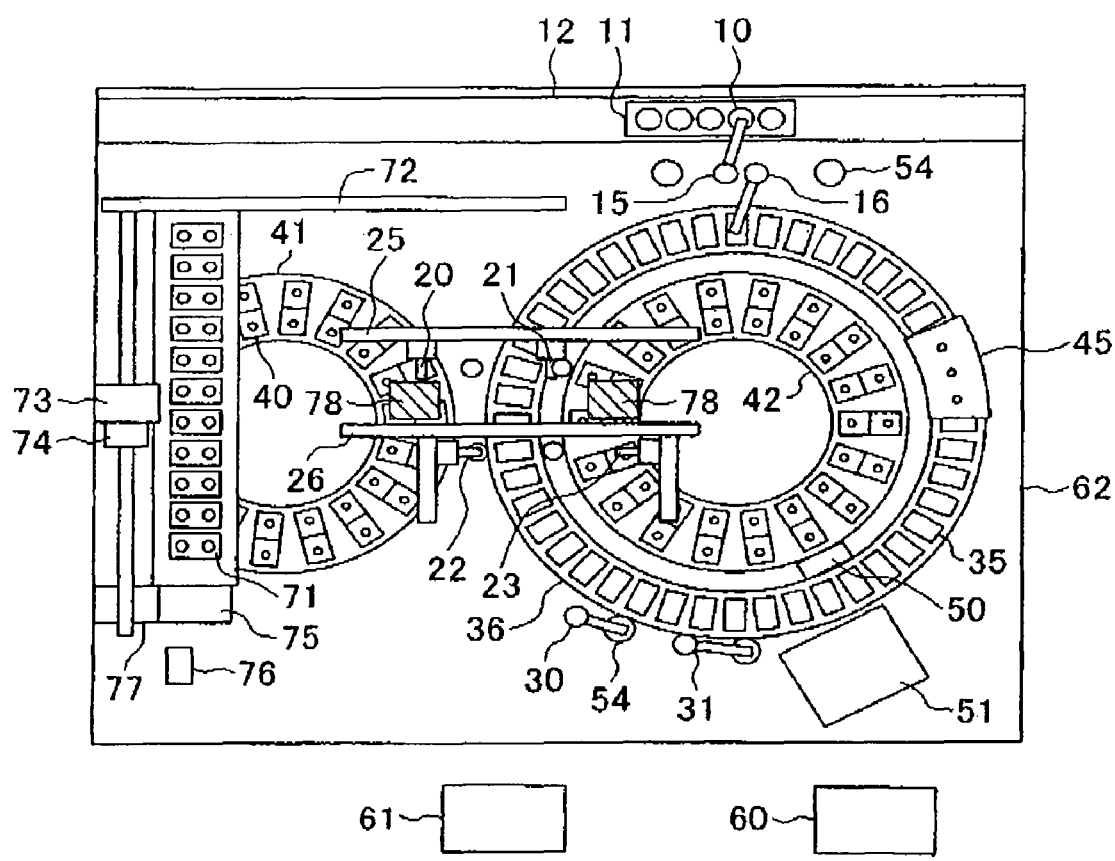
FIG. 1 is a top view of an automatic analyzer according to a first embodiment of the present invention.

FIG. 1 is a top view of an automatic analyzer having a supplemental reagent container storage case, according to a first embodiment of the present invention. Referring to FIG. 1, in a cabinet 62, a plurality of reaction vessels 35 is regularly arranged along the circumference of a reaction disk 36 that is rotatable in one direction. A reagent disk 42 is disposed inside the reaction disk 36 while a reagent disk 41 is disposed outside the reaction disk 36. Each of the reagent disks 41 and 42 is arranged rotatably in opposite directions, and is adapted so as to be rotated in a direction such that the rotational angle necessary to convey a required reagent to the respect one of reagent probes 20 and 21 is smaller. Reagent containers 40 can be arranged along the entire circumferences of the reagent disks 41 and 42. The reagent containers 40 contain a plurality of various kinds of reagents respectively, being the first reagent storage means used for the analyzing operation. One reagent container 40 has a structure that contains two regents radially arranged side by side. In the vicinity of the reaction disk 36, there is provided a conveying mechanism 12 for conveying the rack 11 carrying thereon sample containers 10. Rails 25 and 26 are provided above the reagent disks 41 and 42. To the rail 25, there are provided probes 20 and 21 that are movable in the direction parallel to the rail 25 and in the vertical direction. To the rail 26, there are provided probes 22 and 23 that are movable along the rail 26 in the three-axis directions. These reagent probes 20, 21, 22, and 23 are each connected to a pump for reagent, which is not shown.

Sample probes 15 and 16 that are rotatable and vertically movable are provided between the reaction vessels 35 and the conveying mechanism 12. The sample probes 15 and 16 are each connected to a pump for sample, which is not shown. Around the reaction disk 36, there are provided stirrers 30 and 31, a light source 50, a detection optical unit 51, and a vessel cleaning mechanism 45. The vessel cleaning mechanism 45 is connected to a pump for cleaning, which is not shown. A cleaning port 54 is provided in the working area of each of the sample probes 15 and 16, reagent probes 20, 21, 22, and 23, and stirrers 30 and 31.

Above the reagent disk 41, there is provided a supplemental reagent storage case 71, which serves as the second reagent storage means for supplement, in a state where reagent containers are arranged therein in line by twos. The supplemental reagent storage case 71 thus holds a plurality of reagent containers 40. A rail 72 is provided above the supplemental reagent storage case 71. To the rail 72, there are provided reagent holding means 73 and reagent container uncapping means 74 that are movable along the rail 72 in the three axis directions. A reagent container mounting opening 75 is formed in front of the supplemental reagent storage case 71. In the vicinity of the reagent container mounting opening 75, there is provided a barcode reader 76 for reading a reagent barcode. A disposal opening 77 for disposing of reagent caps and used reagent containers 40 is formed in the vicinity of the supplemental reagent storage case 71.

The pump for sample, pump for reagent, and pump for cleaning, which are not shown in the figure; and the detection optical unit 51, reaction vessels 35, reagent disk 41, reagent probes 20, 21, 22, and 23, sample probes 15 and 16, reagent holding means 73, reagent container uncapping means 74, and barcode reader 76 are each connected to a controller 60.

Next, the analysis procedure with the present apparatus will be described. Before starting an analysis, the maintenance of the apparatus is performed. The maintenance of the apparatus includes the checking of the detection optical unit 51, the cleaning of the reaction vessels 35, the cleaning of various probes such as the sample probes 15 and 16. In addition, and most importantly, the maintenance of the apparatus includes the checking of reagents to be used for analysis and contained in the reagent containers 40 that are mounted on the reagent disks 41 and 42. Regarding information about the reagent containers 40, the mounted positions, lot numbers, expiration dates, remaining reagent amounts, and the like of reagents in the reagent disks 41 and 42, are stored in a control computer 61. The operator checks conditions of the reagent containers in the reagent disks 41 and 42 by a cathode-ray tube (CRT; not shown) or the like. Reagents of which the remaining amount are slight and which might become empty in course of analysis in a day are set in the reagent container mounting opening 75. The set reagent, of which the reagent information is read by the barcode reader 76, is conveyed to the supplemental reagent storage case 71 by the reagent holding means 73. The read reagent information and the information on the mounted position of the reagent in the supplemental reagent storage 71 are outputted to the control computer 61. The maintenance of all reagents supposed to become deficient is performed by the above-described procedure.

The sample container 10 is loaded with a sample to be examined, such as blood, urine, or the like, and after being mounted onto the rack 11, it is conveyed by the transfer mechanism 12. The sample taken by the sample probe 15 is dispensed in a definite amount into the reaction vessel 35 disposed on the reaction disk 36, and then a definite amount of regent is dispensed by the reagent probe 21 or 22 from the reagent container 40 disposed on the reagent disk 41 or 42 into the reaction vessel 35. The mixture of the sample and reagent is stirred by the stirrers 30 and 31. After the mixture has been subjected to a reaction for a definite time, the absorbance, spectrum, and the like of the reaction vessel 35 is measured by the detection optical unit 51. The measurement result is outputted to the control computer 61. If further measurement items have been requested, the above-described sampling is repeated. Likewise, regarding all samples on the rack 11, the sampling is repeated until the sampling with respect to the set measurement items is completed.

When a reagent in the reagent disk 41 or 42 is likely to become deficient in course of analysis, a reagent supplement is performed by the following procedure. Since the data on the remaining amount of the reagent in the reagent disk 41 or 42 is stored in the control computer 61, it is known in advance how many measurements left is to cause the deficiency of the reagent. Also, the data on the number of pertinent items requested of the apparatus is also stored by the control computer. These enable the reagent to be supplemented before the deficiency of the reagent is caused.

Because the reagent that is required to be supplemented has been loaded in advance on the supplemental reagent storage case 71, it is to be carried into the reagent disk 41 or 42 from the supplemental reagent storage case 71 by the reagent holding means 73. For this purpose, firstly, the reagent holding means 73 takes out the required reagent from the supplemental reagent storage case 71, and places it once in the reagent container mounting opening 75. Then, the reagent barcode is read by the barcode reader 76, and it is checked whether the reagent is the pertinent reagent. If the reagent is the pertinent one, the reagent container 40 is uncapped by the reagent container uncapping means 74. The opened cap is thrown away into the disposal opening 77. Then, the reagent disk 41 or 42 is rotated so as to stand by with a designated disposition position aligned with the reagent mounting opening 78. The uncapped reagent container 40 is conveyed to the reagent mounting opening 78 by the reagent holding means 73, and mounted on the reagent disk 41 or 42.

Regarding the timing of reagent mounting, as long as a reagent deficiency is not caused, the mounting of reagent container is performed by making use of a free cycle during a sample-to-sample interval, the time interval between a first reagent dispensing and a second reagent dispensing, or the like. However, if the reagent mounting cannot possibly performed in time for the supplementation of a reagent, the sampling is interrupted, and the reagent mounting is performed after the completion of the reagent dispensing into the sample that was performed before the sampling interruption. In any case, the apparatus is in a state of continuing an analysis, and the supplementation of reagent is performed without temporarily interrupting the apparatus, thereby cutting down the time of analysis interruption.

The supplemented reagent container 40 starts to be used from the time when the apparatus determines a reagent that is likely to become deficient as being deficient. Here, "being deficient" as determined by the apparatus does not mean that the reagent is now deficient in a literal sense, but means that a more use of the reagent might make a normal analysis impossible. In reality, the reagent container 40 has a small amount of the reagent left therein. If it is determined that a calibration curve has not to be re-created because the lot of the supplemented reagent is the same as that of the original reagent, the supplemented reagent can be used as it is. On the other hand, when the re-creation of the calibration curve is needed, a required standard solution is conveyed as a sample by the rack 11, and after a calibration curve has been re-created, the reagent is used.

Meanwhile, at the timing of the mounting of supplemental reagent or at any timing out of the above-described timings, the used reagent container 40 is discharged from the reagent disk 41 or 42, and conveyed to the disposal opening 77 to throw away thereinto by the reagent holding means 73.

As described above, the present embodiment includes the reagent storage means for supplement and reagent container conveying means in addition to the reagent storage means for analysis. This makes it possible to reduce the burden of reagent management imposed on the operator, minimize the analysis interruption due to the reagent registration and reagent replacement, load a large number of reagents, and achieve a high throughput.

Second Embodiment

Figure 2:
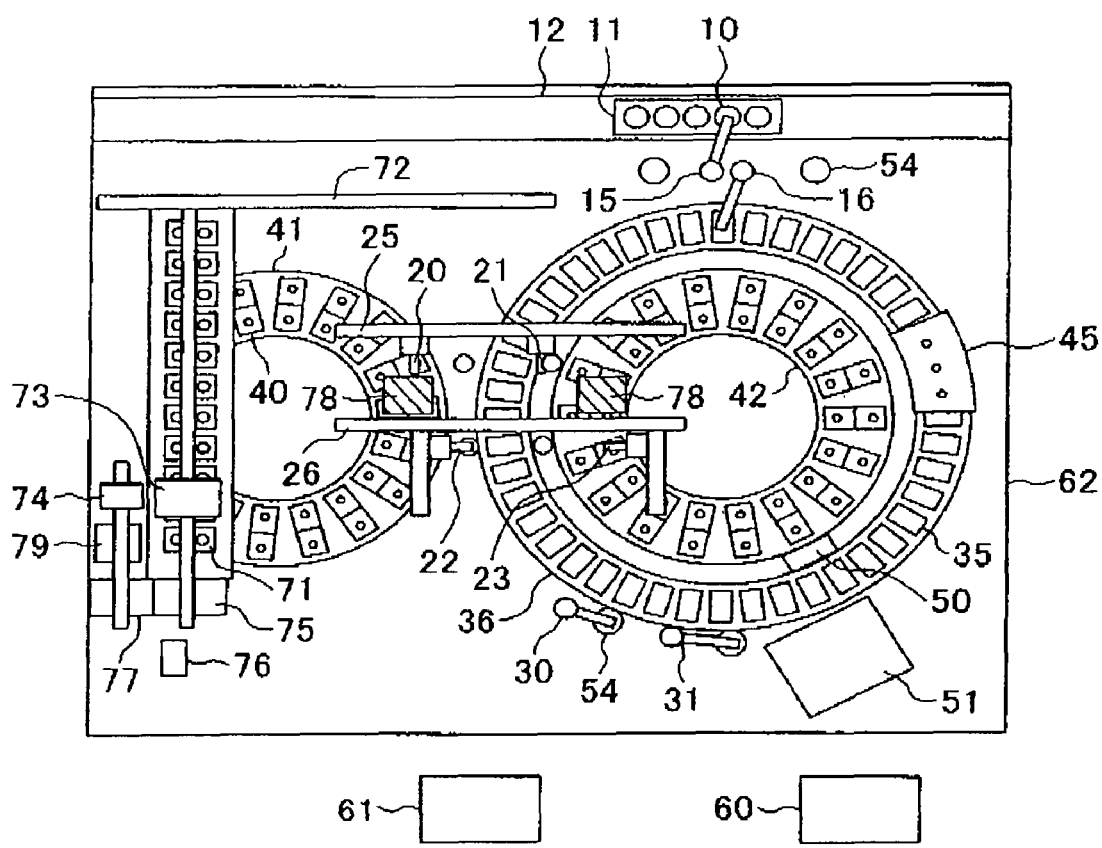
FIG. 2 is a top view of an automatic analyzer according to a second embodiment of the present invention.

FIG. 2 is a top view of an automatic analyzer having a supplemental reagent storage case, according to a second embodiment of the present invention. Here, the reagent holding means 73 and reagent container uncapping means 74 above the supplemental reagent storage case 71 are disposed and driven independently of each other. Also, an uncapping position 79 is independently provided. In this embodiment, while performing uncapping operation, the conveyance of a reagent container 40 that is subsequently to be mounted on the reagent disk, or the mounting of a new reagent on the supplemental reagent storage case 71 can be performed, thereby enabling a more efficient supplementation of reagent.

In this embodiment also, it is possible to lighten the burden of reagent management imposed on the operator, minimize the analysis interruption due to the reagent registration and reagent replacement, load a large number of reagents, and implement a high throughput.

Third Embodiment

Figure 3:
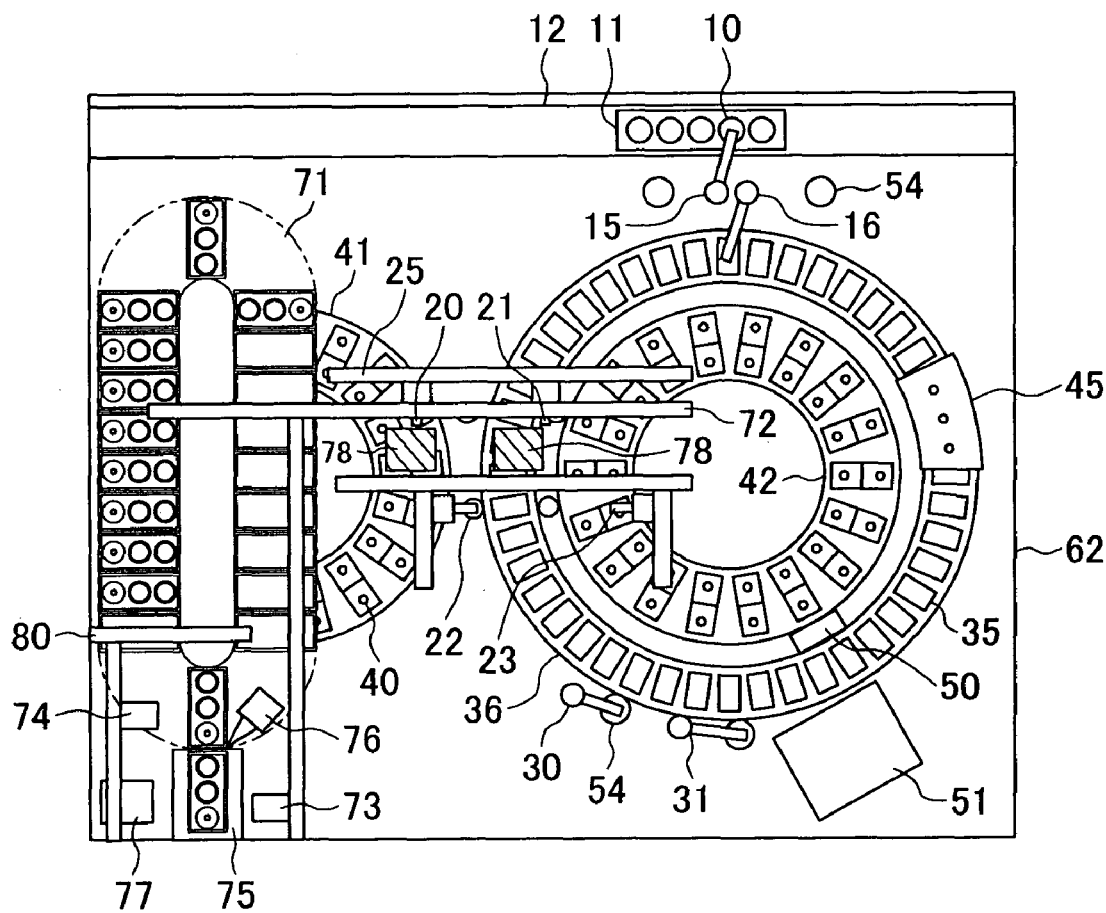
FIG. 3 is a top view of an automatic analyzer according to a third embodiment of the present invention.

FIG. 3 is a top view of an automatic analyzer having a supplemental reagent storage case, according to a second embodiment of the present invention. A supplemental reagent storage case 71, serving as the second reagent storage means, is disposed above the reagent disk 41. The supplemental reagent storage case 71 can mount thereon a plurality of reagent containers 40. A rail 72 is provided above the supplemental reagent storage case 71 and the reagent disk 42. To the rail 72, there is provided reagent holding means 73 that is movable along the rail 72 in the three axis directions. Also, a rail 80 is provided above the supplemental reagent storage case 71. To the rail 80, there is provided reagent container uncapping means 74 that is movable along the rail 80 in the three axis directions. A reagent container mounting opening 75 is formed in front of the supplemental reagent storage case 71. In the vicinity of the reagent container mounting opening 75, there is provided a barcode reader 76 for reading a reagent barcode. A disposal opening 77 for disposing of reagent caps and used reagent containers 40 is formed in the vicinity of the supplemental reagent storage case 71.

Next, the reagent introducing method and reagent container disposal method using the supplemental reagent storage case 71 will be described. The operator sets the reagent container 40 in the reagent container mounting opening 75. The set reagent container 40 is conveyed to the supplemental reagent storage case 71 by the reagent holding means 73. While the reagent container 40 is conveyed from the reagent container mounting opening 75 to the supplemental reagent storage case 71, the reagent information adhered thereto is read by the barcode reader 76. The read reagent information and the information on the mounted position of the reagent container 40 in the supplemental reagent storage 71 are outputted to the control computer 61. Here, the supplemental reagent storage case 71 is arranged to be rotationally drivable in an annular manner. The above-described work is repeated to mount required reagents on the supplemental reagent storage case 71. The procedure for carrying the reagent container 40 into the reagent disk 41 or 42 will be described below.

The reagent container 40 required to be supplemented is to be carried into the reagent disk 41 or 42 from the supplemental reagent storage case 71 by the reagent holding means 73. For this purpose, firstly, the supplemental reagent storage case 71 is rotated so that the reagent container 40 required to be supplemented stands by at the position facing the reagent container mounting opening 75. The reagent container 40 is once placed in the reagent container mounting opening 75 by the reagent holding means 73. The reagent barcode is read by the barcode reader 76, and it is checked whether the reagent is the pertinent reagent. If the reagent is the pertinent one, the reagent container 40 is uncapped by the reagent container uncapping means 74. The opened cap is thrown away into the disposal opening 77.

Then, the reagent disk 41 or 42 is rotated so as to stand by with a designated disposition position aligned with the reagent mounting opening 78. The uncapped reagent container 40 is conveyed to the reagent mounting opening 78 by the reagent holding means 73, and mounted on the reagent disk 41 or 42. Considering that the orientation of the reagent container 40 at this time is different from the orientation at the time when it has been placed in the reagent container mounting opening 75, the reagent holding means 73 is arranged to have a mechanism capable of rotating. Since the reagent holding means 73 has such a rotating mechanism, the reagent mounting opening 78 can be disposed at an arbitrary angle with respect to the reagent disk 41 or 42, in accordance with the relationship with other mechanisms.

On the other hand, the reagent container 40 that has become empty in the reagent disk 41 or 42 is discharged by the following procedure. The reagent disk 41 or 42 is rotated so as to stand by with the empty reagent container 40 aligned with the reagent mounting opening 78. The reagent holding means 73 takes out the reagent container 40 from the reagent mounting opening 78, and after directly moving to the disposal opening 77, throws away the reagent container 40 thereinto.

Because the supplemental reagent storage case 71 according to this embodiment is rotationally drivable, and its drive section can be controlled with a single shaft, it can be more easily controlled than the supplemental reagent storage case 71 according to the first and second embodiments. Also, according to this embodiment, it is possible to reduce the burden of reagent management imposed on the operator, minimize the analysis interruption due to reagent registration and reagent replacement, load a large number of reagents, and achieve a high throughput.

Fourth Embodiment

Figure 4:
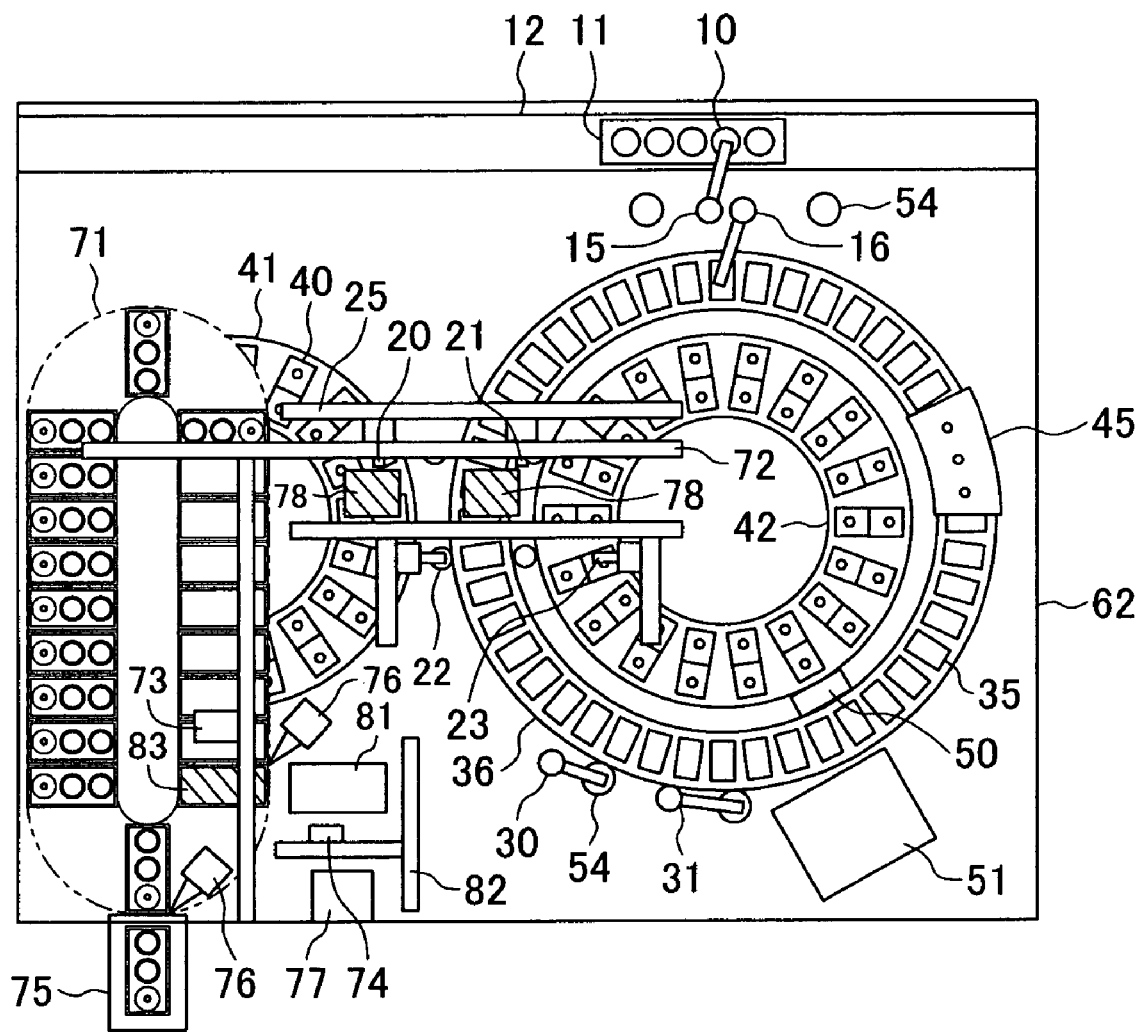
FIG. 4 is a top view of an automatic analyzer according to a fourth embodiment of the present invention.

FIG. 4 is a top view of an automatic analyzer having a supplemental reagent storage case, according to a second embodiment of the present invention. A supplemental reagent storage case 71, serving as the second reagent storage means, is disposed above the reagent disk 41. The supplemental reagent storage case 71 can mount thereon a plurality of reagent containers 40. A rail 72 is provided above the supplemental reagent storage case 71 and the reagent disk 42. To the rail 72, there is provided reagent holding means 73 that is movable along the rail 72 in the three axis directions. A rail 82 is provided above the supplemental reagent storage case 71. To the rail 82, there is provided reagent container uncapping means 74 that is movable along the rail 82 in the three axis directions. A reagent container mounting opening 75 is formed in front of the supplemental reagent storage case 71. In the vicinity of the reagent container mounting opening 75, there is provided a barcode reader 76 for reading a reagent barcode. A disposal opening 77 for disposing of reagent caps and used reagent containers 40 is formed in the vicinity of the supplemental reagent storage case 71. Also, in the vicinity of the supplemental reagent storage case 71, there is provided a reagent container uncapping port 81, which is a dedicated port for uncapping the reagent container.

Here, the reagent introducing method and reagent container disposal method using the supplemental reagent storage case 71 will be described. The operator sets the reagent container 40 in the reagent container mounting opening 75, and pushes it into the supplemental reagent storage case 71 by hand, or by a mechanism for pushing-in 61. At this time, reagent information is read by the barcode reader 76. The read reagent information and the information on the mounted position of the reagent container 40 in the supplemental reagent storage 71 are outputted to the control computer 61. Here, the supplemental reagent storage 71 is the same as that used in the third embodiment.

The procedure for carrying the reagent container 40 into the reagent disk 41 or 42 is described below. The reagent container 40 required to be supplemented is to be carried into the reagent disk 41 or 42 from the supplemental reagent storage case 71 by the reagent holding means 73. For this purpose, firstly, the supplemental reagent storage case 71 is rotated so that the reagent container 40 required to be supplemented stands by at the reagent container carrying-out opening 83. The reagent container 40 is conveyed from the supplemental reagent storage case 71 to the reagent container uncapping port 81 by the reagent holding means 73. At this time, the reagent barcode is read by the barcode reader 76, and it is checked whether the reagent is the pertinent reagent. If the reagent is the pertinent one, the reagent container 40 is uncapped by the reagent container uncapping means 74. The opened cap is thrown away into the disposal opening 77. Then, the reagent disk 41 or 42 is rotated so as to stand by with a designated disposition position aligned with the reagent mounting opening 78. The uncapped reagent container 40 is conveyed to the reagent mounting opening 78 by the reagent holding means 73, and mounted on the reagent disk 41 or 42. The reagent container 40 that has become empty in the reagent disk 41 or 42 is discharged by the same procedure as that in the third embodiment.

According to this embodiment, since the reagent container holding mechanism 73 requires no rotation mechanism, a simpler supplemental reagent storage case 71 than that in the third embodiment can be provided. Also, since the present embodiment includes the reagent storage means for supplement and reagent container conveying means in addition to the reagent storage means for analysis, it is possible to reduce the burden of reagent management, imposed on the operator, minimize the analysis interruption due to reagent registration and reagent replacement, load a large number of reagents, and achieve a high throughput.

Fifth Embodiment

Figure 5A:
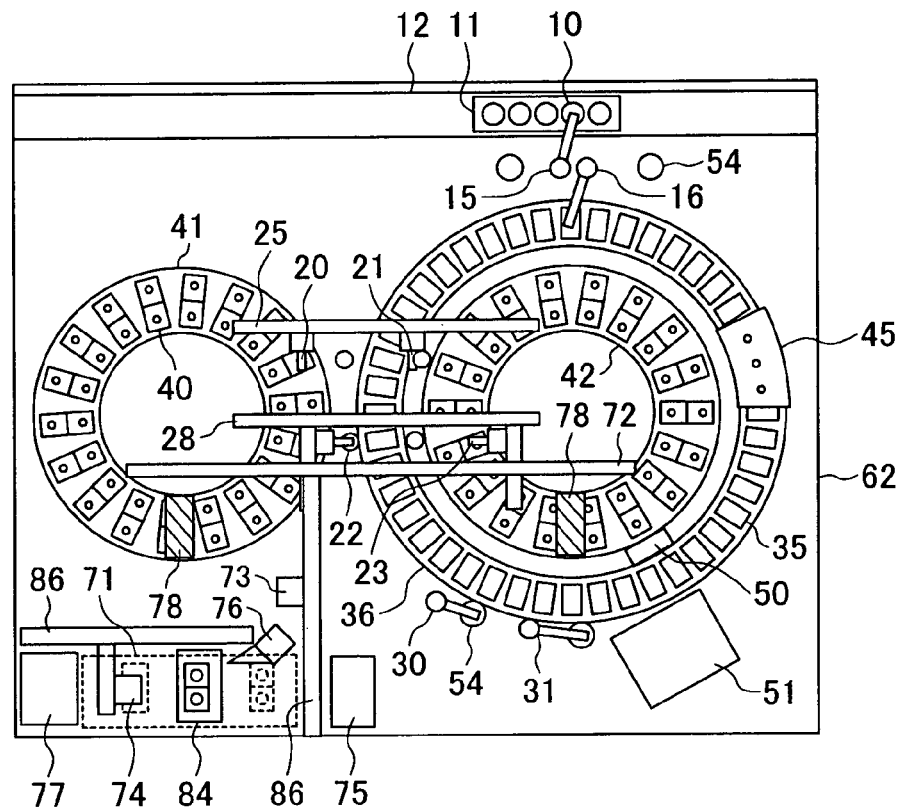
FIG. 5A is a top view of an automatic analyzer according to a fifth embodiment of the present invention.
Figure 5B:
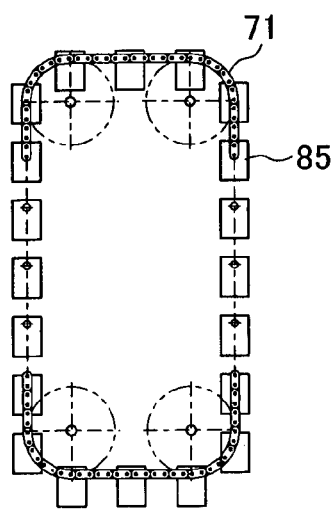
FIG. 5B is a front view of a supplemental reagent storage case in the automatic analyzer according to this embodiment.

FIG. 5A is a top view of an automatic analyzer having a supplemental reagent storage case, according to a second embodiment of the present invention, and FIG. 5B is a front view of this supplemental reagent storage case as viewed from the side of the automatic analyzer. The supplemental reagent storage case 71 is either provided so as to be imbedded in the apparatus in front of the reagent disk 41, or mounted on the front surface of the apparatus. The supplemental reagent storage case 71 can mount thereon a plurality of reagent containers 40. A rail 72 is provided above the reagent disks 41 and 42. To the rail 72, there is provided reagent holding means 73 that is movable along the rail 72 in the three axis directions. A rail 86 is provided in front of the supplemental reagent storage case 71. To the rail 86, there is provided reagent container uncapping means 74 that is movable along the rail 86 in the three axis directions. In the vicinity of the reagent holding means 73, a reagent container mounting opening 75 is formed. In the vicinity of the reagent container carrying-in/out opening 84, there is provided a barcode reader 76 for reading a reagent barcode. A disposal opening 77 for disposing of reagent caps and used reagent containers 40 is formed in the vicinity of the reagent container uncapping means 74.

The reagent introducing method and reagent container disposal method using the supplemental reagent storage case 71 is described below. The operator sets the reagent container 40 in the reagent container mounting opening 75. The set reagent container 40 is conveyed to the reagent container carrying-in/out opening 84 by the reagent holding means 73. At this time, reagent information is read by the barcode reader 76. The read reagent information and the information on the mounted position of the reagent container 40 in the supplemental reagent storage 71 are outputted to the control computer 61. As shown in FIG. 5B, the supplemental reagent storage 71 has a structure that is capable of rotating in the direction perpendicular to the plane of the figure in a state where it is supported by four pulleys and a chain, and that includes a plurality of reagent container baskets 85 for storing the conveyed reagent container 40.

The procedure for carrying the reagent container 40 into the reagent disk 41 or 42 is described below. The reagent container 40 required to be supplemented is to be carried into the reagent disk 41 or 42 from the supplemental reagent storage case 71 by the reagent holding means 73. For this purpose, firstly the supplemental reagent storage case 71 is rotated so that the reagent container 40 required to be supplemented stands by at the reagent container carrying-in/out opening 84. Here, the reagent barcode is read by the barcode reader 76, and it is checked whether the reagent is the pertinent reagent. If the reagent is the pertinent one, the reagent container 40 is uncapped on the spot by the reagent container uncapping means 74. The opened cap is thrown away into the disposal opening 77. Then, the reagent disk 41 or 42 is rotated so as to stand by with a designated disposition position aligned with the reagent mounting opening 78. The uncapped reagent container 40 is conveyed from the reagent container carrying-in/out opening 84 to the reagent mounting opening 78 by the reagent holding means 73, and mounted on the reagent disk 41 or 42. The reagent container 40 that has become empty in the reagent disk 41 or 42 is discharged by the same procedure as that in the third embodiment.

In the supplemental reagent storage case 71 according to this embodiment, since the reagent containers 40 are arranged in the vertical direction and rotationally driven along the up-and-down direction, a supplemental reagent storage case having an improved space efficiency can be provided. Moreover, it is possible to reduce the burden of reagent management imposed on the operator, minimize the analysis interruption due to the reagent registration and reagent replacement, load a large number of reagents, and achieve a high throughput.

As is evident from the foregoing, according to the present invention, it is possible to provide an automatic analyzer that reduces burden imposed on the operator, such as reagent registration and reagent replacing operations, and that eliminates the deficiency of reagent in amount during analysis, thereby minimizing the interruption of an analysis.

What is claimed is:

1. An automatic analyzer system that dispenses samples and reagents into each of a plurality of reaction vessels to allow them to react with each other, and that measures the liquids formed as a result of the reactions, the automatic analyzer system comprising:
    a reaction disk containing said plurality of reaction vessels;
    first reagent storage disks for storing first reagent containers holding reagents to be used for the reactions, where one of said first reagent storage disks is disposed outside of said reaction disk and another of said first reagent storage disks is disposed inside of said reaction disk;
    a second reagent storage case, disposed above said one of said first reagent storage disks, for storing a plurality of second reagent containers holding reagents, said plurality of second reagent containers being supplemented to said first reagent containers, said plurality of second reagent containers hold a number of different reagents;
    a reagent holding means for conveying said plurality of second reagent containers from the second reagent storage case to the first reagent storage disks;
    a reader for reading information provided on each of the plurality of second reagent containers; and
    a controller for controlling said reagent holding means;
    a control computer storing reagent information read by said reader of each of said plurality of second reagent containers added to said second reagent storage case and information on the position where the added said second reagent containers are placed in said second reagent storage case,
    said control computer storing a mounted position and a remaining reagent amount of each of reagents in a plurality of first reagent containers on said first reagent storage disks,
    said control computer operates to cause said reader to check the reagent information of one of said plurality of second reagent containers holding a reagent to be supplemented, said controller operates said reagent holding means to convey the checked said one of said plurality of second reagent containers, if verified to hold the reagent to be supplemented, to said first reagent storage disks, and said control computer operates to determine whether or not a normal analysis can be performed with an amount of reagent remaining in said first reagent containers stored in the first reagent storage disks and, if not, said controller operates said reagent holding means to convey said one of said plurality of second reagent containers from the second storage case to the first reagent storage disks.

2. The automatic analyzer system according to claim 1, wherein the reagent holding means conveys one of said first reagent containers that has been used in the first reagent storage disks to the second reagent storage case.

3. The automatic analyzer system according to claim 1, wherein the second reagent storage case or the reagent holding means has an opening portion for discharging said first or second said reagent containers to the outside.

4. The automatic analyzer according to claim 1, wherein the second reagent storage case has a cold-storage.

5. The automatic analyzer system according to claim 1, wherein the first reagent containers are disposed along an outer periphery of one of said first reagent storage disks side by side in the radial direction of the one first reagent storage disk by twos or more.

6. The automatic analyzer system according to claim 1, wherein the second reagent storage case holds a plurality of said second reagent containers that are arranged in line by twos or more.

7. The automatic analyzer system according to claim 1, wherein the second reagent storage case holds a plurality of said second reagent containers arranged in an annular manner by twos or more.

8. The automatic analyzer system according to claim 1, wherein the second reagent storage case holds the plurality of said second reagent containers so as to be rotationally drivable in the vertical direction.

9. The automatic analyzer system according to claim 1, wherein the first reagent containers mounted on one of the first reagent storage disks are disposed along an outer periphery of the one first reagent storage disk in a state where they are arranged side by side in the radial direction of the first reagent storage disk by twos or more.

10. The automatic analyzer system according to claim 1, wherein the second reagent storage case is configured to hold said second reagent containers in a line arrangement of twos or more.

11. The automatic analyzer system according to claim 1, wherein the second reagent storage case is rotationally drivable, and is configured to hold therein a plurality of said second reagent containers in an annular arrangement by twos or more.

12. The automatic analyzer system according to claim 1, wherein the second reagent storage case is provided on a side portion of the one of said first reagent storage disks that and is rotationally drivable in the vertical direction, the second reagent storage case configured to hold therein a plurality of said second reagent containers in an annular arrangement by twos or more.

* * * * *